United States Patent [19]
Gray, Jr.

[11] Patent Number: 5,495,719
[45] Date of Patent: Mar. 5, 1996

[54] METHOD OF PRESERVING SPERMATOZOA

[76] Inventor: Carl O. Gray, Jr., 14240 Fancher Rd., Johnstown, Ohio 43031

[21] Appl. No.: 338,365

[22] Filed: Nov. 14, 1994

[51] Int. Cl.$^6$ .................................................. F25D 17/02
[52] U.S. Cl. ...................................... 62/78; 62/64
[58] Field of Search ............................................ 62/64, 78

[56] References Cited

U.S. PATENT DOCUMENTS

| | | | |
|---|---|---|---|
| 3,431,172 | 3/1969 | Rajamannan | 195/1.8 |
| 3,791,384 | 2/1974 | Richter et al. | 128/260 |
| 3,816,249 | 6/1974 | Bhattacharya | 195/1.8 |
| 3,940,943 | 3/1976 | Sikes et al. | 62/64 |
| 3,952,536 | 4/1976 | Faust et al. | 62/293 |
| 3,973,003 | 8/1976 | Colas | 424/105 |
| 4,251,995 | 2/1981 | Pert et al. | 62/60 |
| 4,630,448 | 12/1986 | Bilstad et al. | 62/60 |
| 4,865,871 | 9/1989 | Livesey et al. | 427/4 |

Primary Examiner—Ronald C. Capossela
Attorney, Agent, or Firm—John L. Gray

[57] ABSTRACT

Applicant has found that by freezing spermatozoa, especially stallion spermatozoa, in an extender in a flat container having a thickness so that the frozen product does not exceed 4 mm thickness results in a significant increase in the number of spermatozoa surviving upon thawing.

4 Claims, 1 Drawing Sheet

METHOD OF PRESERVING SPERMATOZOA

BACKGROUND OF THE INVENTION

It is common to preserve blood, body tissue, and semen by freezing. Example of methods and devices used for the freezing and storing of blood and body tissue are illustrated in U.S. Pat. No. 4,630,448, Bilstad, et al., U.S. Pat. No. 3,952,536, Faust, et al., U.S. Pat. No. 4,251,995, Pert, et al., U.S. Pat. No. 3,431,172, Rajamannam, and U.S. Pat. No. 4,865,871, Livesey, et al.

However, the freezing of spermatozoa involves entirely different problems than those faced in connection with the freezing of blood or tissue. Blood and tissue are not as easily damaged during the freezing or subsequent thawing process as are spermatozoa.

The three functions that are particularly critical and specific to spermatozoa are (1) the innate ability of spermatozoa to locate the ovum, (2) the self mobilization of the spermatozoa, and (3) the ability of the spermatozoa to attach to the ovum and enter through barriers to fertilize the ovum.

The ability of the spermatozoa to move from the cervix to the ovum located high in the ovaduct is a very specialized function that is easily disrupted by changes in temperature. Other cells that are preserved by freezing (i.e., blood cells), depend on cardiovascular circulation to transport them where they are needed.

The spermatozoa has a tail that rotates so that the cell is moved in a straightforward direction. When a spermatozoa is cooled too rapidly without proper preparation and the use of extenders, the motility apparatus in the tail may be damaged to change the motility of the spermatozoa. Even a slight change in the motility can result in the spermatozoa moving in circles or to inhibit its motility completely. In either case the spermatozoa are incapable of reaching the ovum and achieving fertilization.

The spermatozoa has the ability to enter the ovum after crossing three barriers (cumulus cells, zona pellucida, and the ovum's cell membrane). To accomplish this task it requires the motility generated by the tail and special enzymes located at the head of the spermatozoa under a membrane referred to as the acrosomal cap. The acrosomal cap is dissolved away shortly before the spermatozoa reaches the ovum. The process is referred to as capacitation. If the acrosomal cap is damaged during the freezing process, then the enzymes may be released too soon, or the cap may be unable to undergo capacitation. There has also been speculation that under the acrosomal cap there may be specialized receptors that enable the spermatozoa to attach to the ovum's cell membrane and allow entrance into the ovum. This is referred to as fertilization. How the cooling, freezing, and thawing techniques affect this final step is still unknown.

Examples in the prior art of patents relating to the process for the preservation of semen are set forth in U.S. Pat. No. 3,973,003, Colas, U.S. Pat. No. 3,816,249, Bhattacharya, U.S. Pat. No. 3,791,384, Richter, et al., and U.S. Pat. No. 3,940,943, Sikes, et al.

Currently spermatozoa for use in the insemination of such animals as horses and cattle are preserved frozen in straws that are less than 4 mm in diameter. In preparing semen for freezing it is common practice to add a diluent, then centrifuge the mix to remove seminal plasma. Thereafter the semen is mixed with cryoprotectant or an extender that protects the semen to some extent during the freezing and thawing process.

The disadvantage of the use of straws to preserve frozen spermatozoa, which is the current state of the art, is that the spermatozoa must be either packaged so concentrated so as not to allow enough extender to be incorporated to properly protect the spermatozoa during freezing, or multiple straws must be used to inseminate the female. As a practical matter, this technique is only successful in species where a low number of spermatozoa are sufficient to provide fertility such as in cattle.

Another disadvantage of the use of straws is the temperature to thaw the semen to retain fertility is relatively high, even though the time required to thaw the sample may be short (75° C. for 7.0 seconds). It has long been established that temperatures above body temperature (37° C.) decrease the longevity of spermatozoa. Faulkner, et al. *Artificial Insemination in Veterinarian Endocrinology and Reproduction*, edited by L. E. McDonald, 2nd edition 1977, described the thermal limit of spermatozoon's viability from 50° C. to temperatures below −196° C. (with cryoprotectants). Therefore, the outer layers of spermatozoa may undergo thermal damage and be unable to achieve fertility. After the spermatozoa are thawed with the high temperature, the sample must be rushed to the female for insemination to reduce the recooling of the spermatozoa as this may result in damage to the spermatozoa.

SUMMARY OF THE INVENTION

Applicant has found that by freezing spermatozoa, especially stallion spermatozoa, with an extender in a flat container having a thickness so that the frozen product does not exceed 4 mm thickness, results in significant increase in the number of spermatozoa surviving upon thawing.

It is therefore an object of this invention to provide a method and an apparatus for freezing spermatozoa wherein the motility of the spermatozoa upon thawing is preserved for a maximum number of spermatozoa in a given frozen batch.

It is a still further object of this invention to provide such a method wherein the thawing of said frozen spermatozoa may be accomplished rapidly and simply with a minimum amount of special equipment and without high temperatures.

These, together with other objects and advantages of the invention will become more readily apparent to those skilled in the art when the following general statements and descriptions are read in the light of the appended drawings.

DETAILED DESCRIPTION OF THE INVENTION

Figure 1:
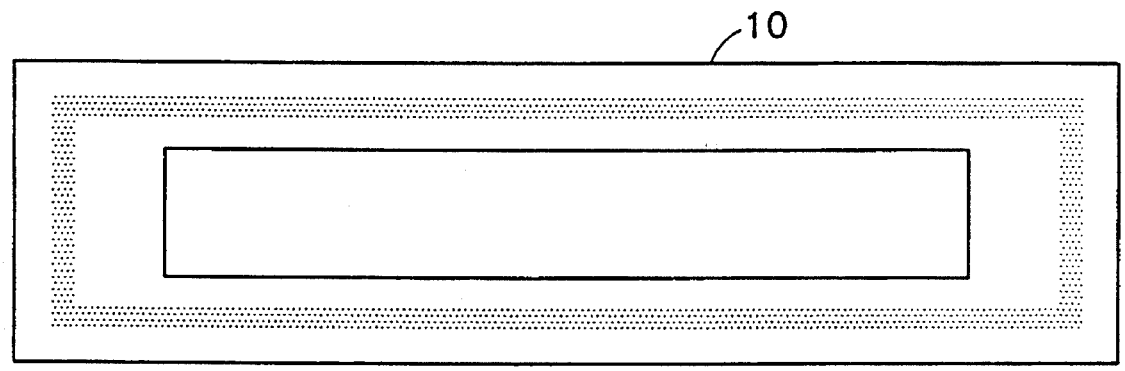
FIG. 1 is a top view of a pouch containing the frozen spermatozoa and extender mixture.
Figure 2:
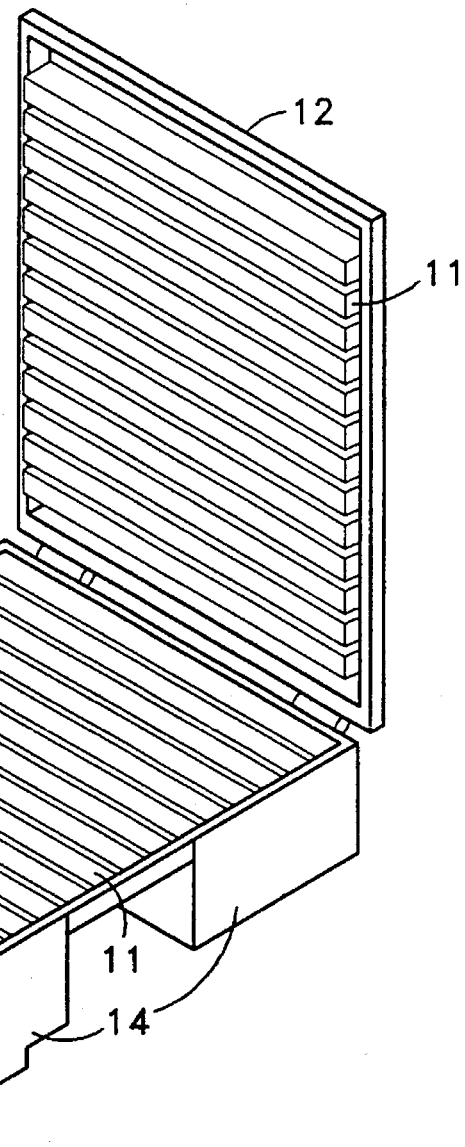
FIG. 2 is a perspective view of the grids holding the pouch in the freezing step.

Referring now more particularly to FIG. 1, there is shown a sealable plastic pouch 10 containing the mixture of frozen spermatozoa and extender. In preparing the semen for freezing, an extender is added and the mixture is then centrifuged to remove seminal plasma. The resultant mixture is mixed with an extender (cryoprotectant) to provide a certain amount of protection to the spermatozoa. The extender and cryoprotectant used are known in the art and this choice will depend upon the particular semen being used and the preference of the individual supervising the process. The mixture is then sealed in the plastic container 10 of FIG. 1 which is then squeezed between two flat metal grids 11-11 as shown in FIG. 2, the cover 12 being closed down on the base 13 so that the resultant frozen mixture will have a maximum thickness which will not exceed 4 mm. The assembly shown in FIG. 2 is then cooled to 5° C. in approximately 15 minutes, and then suspended over liquid nitrogen on styrofoam floats 14-14 for approximately 15 minutes to complete the freezing step. The resultant product is then stored in liquid nitrogen.

The primary advantage of this invention over the prior art is that the semen (in the plastic packets) can be thawed in a waterbath of ambient temperature. The speed of thawing is proportional to the surface area of the semen that has contact to the waterbath. Because the surface area of the packets of semen of this invention is large (as compared to the volume), the semen thaws in less than 15 seconds in a wide range of ambient temperatures (4° C. to 35° C.). The speed of thawing at these wide ranges of temperatures decreases the possibility of frozen sections refreezing the liquid sections of semen, which is detrimental to the semen. Prior art requires temperatures above body temperature (37° C.) which range from 45° C. to 75° C. The timing of thawing semen of prior art is very critical due to the heat damage, which is inevitable to the outer layers of spermatozoa.

After the semen is thawed with other procedures, the temperature is approximately body temperature (37° C.). The semen is then handled with prewarmed instruments to avoid cooling the semen as this is detrimental.

When the frozen semen is thawed with this invention, the temperature is of ambient temperature. Therefore, the instruments may also be of ambient temperature.

The process of the invention is shown in the following examples.

EXAMPLE 1

Stallion semen frozen by this method was thawed in 5° C. temperature waterbath for 15 seconds and was introduced into an infusion pipette at 5° C. for additional insemination of the mare. Fertility was preserved with this method.

EXAMPLE 2

Stallion semen frozen by this method was thawed in a 35° C. waterbath in 7 seconds and was introduced into an infusion pipette at 35° C. for artificial insemination of the mare. Fertility was preserved with this method.

Although fertility rates among species and individuals vary tremendously, semen has been frozen for periods of up to, but not limited to, 72 months with this method with recovery of fertility.

While this invention has been described in its preferred embodiment, it is to be appreciated that variations therefrom may be made without departing from the true scope and spirit of the invention.

What is claimed:

1. A method of preserving spermatozoa which comprises placing a mixture of spermatozoa and a cryoprotectant for said spermatozoa in a flexible flat container, and thereafter freezing said container under restraints so that the thickness of said container, when frozen, will not exceed 4 millimeters.

2. The method of claim 1 wherein said liquid containing said spermatozoa is cooled to a temperature of about 5° C. for approximately 10 minutes prior to freezing.

3. A method of preserving spermatozoa which comprises placing a mixture of spermatozoa and a cryoprotectant for said spermatozoa in a flexible flat container, and thereafter squeezing said flat container between metal grids supported by a material having sufficient buoyancy to support said metal grids and said flat container on liquid nitrogen, thereafter floating said combination of said flat container and said metal grids and said buoyant material on liquid nitrogen for at least 15 minutes or until said spermatozoa are frozen.

4. The method of claim 3 wherein said flat container of frozen spermatozoa is thereafter immersed in liquid nitrogen.

* * * * *